US006361781B2

(12) United States Patent
Lorant

(10) Patent No.: US 6,361,781 B2
(45) Date of Patent: *Mar. 26, 2002

(54) EMULSION COMPRISING A HYDROPHILIC THICKENING COMPOUND AND A LIPOPHILIC THICKENING COPOLYMER, COMPOSITIONS AND PRODUCTS COMPRISING THE EMULSION, AND USES THEREOF

(75) Inventor: Raluca Lorant, Thiais (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/396,405

(22) Filed: Sep. 15, 1999

(30) Foreign Application Priority Data

Sep. 16, 1998 (FR) .......................................... 98 11577

(51) Int. Cl.⁷ ................................................ A61K 7/00
(52) U.S. Cl. ........................ 424/401; 424/64; 514/937
(58) Field of Search ..................... 424/64, 401; 514/937

(56) References Cited

U.S. PATENT DOCUMENTS

| 5,318,995 A | | 6/1994 | Mondet et al. ........... 514/772.1 |
| 5,736,125 A | * | 4/1998 | Morawsky et al. ............ 424/59 |
| 5,879,718 A | * | 3/1999 | Sebillote-Arnaud ......... 424/705 |

FOREIGN PATENT DOCUMENTS

| EP | 0 268 164 | 5/1988 |
| EP | 0 281 360 | 9/1988 |
| EP | 0 406 042 | 1/1991 |
| EP | 0 412 705 | 2/1991 |
| EP | 0 482 417 | 4/1992 |
| EP | 0 708 114 | 4/1996 |
| EP | 0 795 321 | 9/1997 |
| EP | 0 795 322 | 9/1997 |
| EP | 0 795 323 | 9/1997 |
| EP | 0 815 844 | 1/1998 |
| EP | 0 832 645 | 4/1998 |
| WO | WO 96/37180 | 11/1996 |

OTHER PUBLICATIONS

T.G. Majewicz et al., "Oil–Based Cosmetic and Therapueitc Compositions Containing Ethylguar", Research Disclosure, Oct. 1995, p. 642.
English language Derwent Abstract of EP 0 795 321.
English language Derwent Abstract of EP 0 795 322.
English language Derwent Abstract of EP 0 795 323.
English language Derwent Abstract of EP 0 815 844.
English language Derwent Abstract of EP 0 832 645.

* cited by examiner

Primary Examiner—Jose' G. Dees
Assistant Examiner—Konata M. George
(74) Attorney, Agent, or Firm—Finnegan, Henderson, Farabow, Garrett & Dunner, L.L.P.

(57) ABSTRACT

An emulsion comprising an aqueous phase and an oily phase and additionally comprising a hydrophilic thickening compound and a lipophilic thickening copolymer. A cosmetic or dermatological composition comprising, in a cosmetically or dermatologically acceptable medium, such an emulsion. The use of such a combination makes it possible to stabilize an emulsion, in particular an oil-in-water emulsion and more particularly an emulsion not comprising a surfactant.

34 Claims, No Drawings

EMULSION COMPRISING A HYDROPHILIC THICKENING COMPOUND AND A LIPOPHILIC THICKENING COPOLYMER, COMPOSITIONS AND PRODUCTS COMPRISING THE EMULSION, AND USES THEREOF

The present invention relates to a composition which is provided in the form of an emulsion capable of being used in the cosmetics and dermatological fields, in particular for caring for or treating the skin of the body or of the face, more particularly for caring for or treating dry or sensitive skin. The invention also relates to a cosmetic or dermatological composition comprising such an emulsion.

Current cosmetic or dermatological compositions are generally provided in the form of an emulsion of the oil-in-water type (that is to say, a vehicle composed of a continuous aqueous dispersing phase and of a non-continuous oily disperse phase) or of an emulsion of the water-in-oil type (that is to say, a vehicle composed of a continuous fatty dispersing phase and of a non-continuous aqueous disperse phase).

Water-in-oil emulsions therefore comprise a continuous oily phase and make possible the formation, at the surface of the skin, of a lipid film which prevents transepidermal water loss and protects the skin from external attacks. These emulsions are particularly appropriate for protecting and nourishing the skin and in particular for treating dry skin.

Oil-in-water emulsions, for their part, contribute to the skin, on application, a softer, less greasy and lighter feel than water-in-oil emulsions.

Emulsions are generally stabilized by incorporation of emulsifying surfactants of the oil-in-water (O/W) type or of the water-in-oil (W/O) type which, by virtue of their amphiphilic structure, become positioned at the oil/water interface and thus stabilize the dispersed droplets. It is generally necessary to introduce these surfactants in a large amount, which can range up to 10% by weight with respect to the total weight of the emulsion, in order to obtain adequate stability.

In point of fact, these amphiphilic surfactants, used in large amounts, can prove to be irritating to the skin, eyes and/or scalp of the user. Furthermore, their presence at high concentrations can result in non-cosmetic effects, such as a rough, clinging and/or sticky feel, or a compact and heavy final composition. Furthermore, the surfactants must be chosen according to the polarity of the oils and are therefore only compatible with a limited number of oils, thus limiting the variety of the formulations.

Formulators of emulsions are constantly seeking to reduce the content of surfactant in order to improve the harmlessness of the emulsions with regard to the skin, eyes and/or scalp and to improve their cosmetic properties. The main difficulty with which they are generally confronted is to obtain stable emulsions.

Application WO 96/37180 has thus provided a composition capable of applications in the pharmaceutical and/or cosmetics fields which is provided in the form of a "pseudoemulsion" and is devoid of surfactant. The composition comprises, on the one hand, in the aqueous phase, a gelling agent chosen in particular from polyoses or acrylic polymers and, on the other hand, in the fatty phase, a consistency factor chosen from waxy fatty substances and in particular glycerol esters. The consistency factor present in the fatty phase is a substance which is semisolid at 25° C. and has a melting point of greater than 50° C.; it is dissolved under warm conditions in the fatty phase and then recovers its starting semisolid consistency under cold conditions, conferring a degree of consistency and a degree of viscosity on the fatty phase. The composition thus obtained exhibits a microscopic structure different from that of an emulsion.

However, it has been found that, beyond a certain amount of fatty phase, the pseudoemulsion loses stability, under warm conditions and/or over time. This is particularly true for levels of fatty phase of greater than 20% by weight with respect to the total weight of the pseudoemulsion. In point of fact, a high level of fatty phase in an O/W emulsion can prove to be highly advantageous, in particular for cosmetic compositions intended for the care of dry skin. Furthermore, the cosmetic properties of this pseudoemulsion are inadequate: its texture is heterogeneous, its feel greasy, and uptake with the finger is found to be poor.

There therefore still remains the need to have available an O/W emulsion which is stable over time, although it does not comprise a surfactant, and which can comprise a large amount of fatty phase without losing its stability.

The aim of the present invention is to alleviate this need and to provide an emulsion, in particular an O/W emulsion, which can avoid the disadvantages mentioned above and which can be stable while comprising a reduced amount of surfactant and which can tolerate a large amount of fatty phase.

The inventor has found, surprisingly, that it is possible to obtain an emulsion having good cosmetic properties and good stability by using a specific combination of thickeners of the oily phase and of the aqueous phase.

The subject-matter of the present invention is therefore an emulsion comprising an aqueous phase and an oily phase and additionally comprising at least one hydrophilic thickening compound and at least one lipophilic thickening copolymer comprising at least one hydrophobic unit in an amount sufficient to obtain its partial or complete solubility in the oily phase and at least one hydrophilic unit in an amount sufficient to produce thickening of the oily phase; the hydrophilic unit being chosen from $C_3$–$C_6$ monocarboxylic acids with $\alpha,\beta$-ethylenic unsaturation, $C_4$–$C_6$ dicarboxylic acids with $\alpha,\beta$-ethylenic unsaturation, and the monoester or monoamide derivatives of the diacids.

Another subject-matter of the invention is a cosmetic or dermatological composition comprising, in a cosmetically or dermatologically acceptable medium, an emulsion as defined above.

Another subject-matter of the invention is the use of an emulsion as defined above for the cosmetic treatment of the skin, hair, eyelashes, eyebrows, nails, mucous membranes or scalp; in particular, for caring for the face and/or body, making up the face and/or body, removing make-up, or antisun protection.

Another subject-matter of the invention is the use of such an emulsion in the manufacture of a dermatological composition intended for the treatment of the skin, hair, eyelashes, eyebrows, nails, scalp and/or mucous membranes.

Another subject-matter of the invention is a process for the nontherapeutic treatment of the skin, in particular dry and/or sensitive skin, hair, eyelashes, eyebrows, nails, mucous membranes or scalp which comprises applying, to the substrate, such an emulsion or a composition comprising it.

Another subject-matter of the invention is the use of a hydrophilic thickening compound and of a lipophilic thickening copolymer as defined above for stabilizing an emulsion, in particular an oil-in-water emulsion, and more particularly an emulsion not comprising surfactant.

It has been found that the emulsion obtained according to the invention remains stable over time at room temperature or at higher temperatures, despite the low amount, indeed even the absence, of surfactant.

Furthermore, in the case of an oil-in-water emulsion, the fatty phase is completely dispersed in the aqueous phase and makes it possible to obtain a homogeneous composition having the microscopic structure of an emulsion.

The emulsion obtained is easy to apply to the skin, mucous membranes, scalp, hair, eyelashes, eyebrows or nails.

The textures obtained are particularly original: the emulsions are creamy and smooth and are entirely free from the gelled, indeed even gelatinous, appearance of some emulsions of the prior art, the external aqueous phase of which is thickened.

The cosmetic feel on the skin is also appreciated: on application, the emulsion provides a feeling of freshness and of comfort while being rich and nourishing; it is soft and comfortable and not in any way clinging.

The emulsion thus obtained is particularly suited to caring for and treating dry and/or sensitive skin, through the possibility of the presence of a large amount of fatty substance contributing care and comfort and through the absence of irritating surfactant.

Furthermore, the emulsions according to the invention do not require an onerous and expensive procedure, such as a high-pressure homogenization, but can be prepared according to a conventional procedure.

The emulsion according to the invention is preferably provided in the form of an oil-in-water emulsion comprising an internal fatty or oily phase dispersed in an external aqueous phase.

The aqueous phase can comprise water and/or a thermal water and/or a spring water and/or a mineral water and/or a floral water.

The emulsion furthermore comprises at least one hydrophilic thickening compound which can be chosen from any hydrophilic thickener known to a person skilled in the art. Mention may in particular be made of the following compounds:

synthetic polymers,
polysaccharide biopolymers, such as xanthan gum, locust bean gum, guar gum, alginates or modified celluloses, such as hydroxyethylcellulose, methylcellulose, hydroxypropylcellulose and carboxymethylcellulose,
aluminium magnesium silicate;
inorganic thickeners, such as smectites or hectorites, whether modified or unmodified (Bentone or Laponite, for example),
their mixtures.

Mention may be made, among synthetic polymers, of:
(A) polyacrylic acids and in particular:
  (i) poly(glyceryl (meth)acrylate) polymers, such as Hispagel or Lubragel from the companies Hispano Quimica or Guardian,
  (ii) optionally crosslinked acrylic acid homopolymers and copolymers or one of their salts, such as those sold under the name "Carbopol" by the company Goodrich;
(B) polyacrylamide-based polymers and in particular:
  (i) the product sold under the name Sepigel 305 by Seppic, which is composed of an O/W emulsion comprising 35–45% by weight of crosslinked neutralized acrylamide/2-acrylamido-2-methyl-propanesulphonic acid copolymer, 15–25% by weight of isoparaffin hydrocarbons, 3–8% by weight of polyethylene glycol 7EO lauryl ether, and water;
  (ii) acrylate/octylacrylamide copolymers, such as Dermacryl from National Starch;
  (iii) crosslinked polymers of acrylamide and of methacryloyloxyethyltrimethylammonium chloride, such as Salcare SC92 from Allied Colloids;
  (iv) crosslinked polymers of acrylamide and of ammonium acrylate, such as PAS 5161 or Bozepol C from Hoechst;
  (v) crosslinked and virtually or completely neutralized poly(2-acrylamido-2-methylpropane-sulphonic acid) polymers.
(C) copolymers composed of a major fraction of monomeric units originating from monomers chosen from monoolefinically unsaturated $C_3$–$C_6$ carboxylic acids and their anhydrides and of a minor fraction of monomeric units originating from monomers chosen from esters with a fatty chain of acrylic acid monomers, these copolymers optionally being crosslinked.

The crosslinked and virtually or completely neutralized poly(2-acrylamido-2-methylpropanesulphonic acid) polymers which can be used in the context of the invention are water-soluble or swellable in water. They are generally characterized in that they comprise, distributed randomly:

a) from 90 to 99.9% by weight of units of the following formula (1):

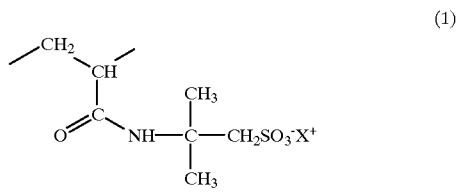

in which $X^+$ is chosen from at least one cation, at most 10 mol % of the $X^+$ cations being able to be $H^+$ protons;

b) from 0.01 to 10% by weight of crosslinking units originating from at least one monomer having at least two olefinic double bonds; the proportions by weight being defined with respect to the total weight of the polymer.

They preferably comprise from 98 to 99.5% by weight of units of formula (1) and from 0.2 to 2% by weight of crosslinking units.

$X^+$ is chosen from at least one cation, the at least one cation being chosen from a proton, alkali metal cations, alkaline earth metal cations, and the ammonium ion. More particularly, 90 to 100 mol % of the cations are $NH_4^+$ cations and 0 to 10 mol % are protons ($H^+$).

The crosslinking monomers having at least two olefinic double bonds are chosen, for example, from dipropylene glycol diallyl ether, polyglycol diallyl ethers, triethylene glycol divinyl ether, hydroquinone diallyl ether, tetraallyloxyethane or other polyfunctional alcohol allyl or vinyl ethers, tetraethylene glycol diacrylate, triallylamine, trimethylolpropane diallyl ether, methylenebisacrylamide or divinylbenzene.

The crosslinking monomers having at least two olefinic double bonds are more particularly chosen from those corresponding to the following general formula (2):

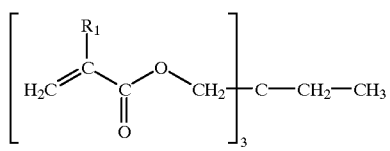

in which $R_1$ is chosen from a hydrogen atom and $C_1$–$C_4$ alkyls and more particularly methyl (trimethylolpropane triacrylate).

These crosslinked polymers can be chosen from those exhibiting a viscosity, measured with a Brookfield viscometer, rotor 4, at a rotational speed of 100 revolutions/minute in a 2% solution in water at 25° C., of greater than or equal to 1000 centipoises, in another embodiment, of a viscosity ranging from 5000 to 40,000 centipoises and in yet another embodiment of a viscosity more particularly from 6500 to 35,000 centipoises.

These polymers are disclosed in particular in Application EP 815,844, the contents of which are explicitly incorporated herein by reference.

It should be noted that this Application EP 815,844 relates to a cosmetic or dermatological composition in the form of an oil-in-water emulsion which is stable while not comprising surfactant and which furthermore comprises a crosslinked poly(2-acrylamido-2-methyl-propanesulphonic acid) polymer neutralized to at least 90%. This polymer is added to the aqueous phase, which it thickens. However, in the composition thus obtained, the fatty phase can only represent up to approximately 12–15% by weight of the emulsion. Beyond this amount of fatty phase, the composition loses stability.

The optionally crosslinked copolymers composed of a major fraction of monomeric units originating from monomers chosen from mono-olefinically unsaturated $C_3$–$C_6$ carboxylic acids and their anhydrides and of a minor fraction of monomeric units originating from monomers chosen from esters with a fatty chain of acrylic acid monomers which can be used in the context of the present invention can be prepared by polymerizing a predominant amount of mono-olefinically unsaturated carboxylic monomer or of its anhydride with a smaller amount of acrylic ester with a fatty chain monomer. The amount of carboxylic monomer or of its anhydride is preferably between 80 and 98%, inclusive, by weight and more particularly between 90 and 98%, inclusive, by weight; the acrylic ester is preferably present in amounts of between 2 and 20%, inclusive, by weight and more particularly between 2 and 10%, inclusive, by weight; the percentages are calculated with respect to the weight of the two monomers.

The preferred carboxylic monomers are chosen from those corresponding to the formula: $CH_2=CR-COOH$, in which R is chosen from a hydrogen, halogens, a hydroxyl, a lactone group, a lactam group, a cyanogen group (—CN), monovalent alkyl groups, aryl groups, alkylaryl groups, aralkyl groups and cycloaliphatic groups.

The particularly preferred carboxylic monomers are chosen from acrylic acid, methacrylic acid, maleic anhydride and their mixtures.

The acrylic ester with a fatty chain monomers are preferably chosen from those corresponding to the formula: $CH_2=CR^1-COOR^2$ in which $R^1$ is chosen from hydrogen, methyl and ethyl and $R^2$ is chosen from $C_8$–$C_{30}$ alkyl groups, $C_8$–$C_{30}$ oxyalkylene groups and carbonyl($C_8$–$C_{30}$ oxyalkylene) groups.

The particularly preferred ester monomers are those in which $R^1$ is chosen from hydrogen and methyl and those in which $R^2$ is chosen from $C_{10}$–$C_{22}$ alkyl groups. Mention may in particular be made of decyl, lauryl, stearyl, behenyl or melissyl acrylates and methacrylates.

Some of these copolymers are disclosed in particular in Application EP-A-0,268,164, the disclosure of which is specifically incorporated by reference herein and are obtained according to the preparation methods disclosed in this same document.

Mention may more particularly be made of the copolymers sold under the name Pemulen by the Company Goodrich and in particular the acrylate/$C_{10}$–$C_{30}$ alkyl acrylate copolymer, such as the product Pemulen TR 2.

In the context of the present invention, use may very clearly be made of a mixture of several hydrophilic thickeners as defined above.

The hydrophilic thickeners can be present in the cosmetic or dermatological compositions of the invention in concentrations generally ranging from 0.05 to 10% by weight with respect to the total weight of the composition and, in another embodiment, 0.5 to 4% by weight.

The viscosity of the aqueous phase is generally of the order of 30,000 to 80,000 centipoises (30–80 Pa·s), measured with a Brookfield viscometer, needle 7, at a speed of 20 revolutions/minute.

The emulsion according to the invention furthermore comprises an oily phase which comprises at least one lipophilic thickening copolymer chosen from copolymers comprising at least one hydrophobic unit in an amount sufficient to obtain their partial or complete solubility in the oily phase and at least one hydrophilic unit in an amount sufficient to produce thickening of the oily phase; the hydrophilic unit being formed from entities chosen from $C_3$–$C_6$ monocarboxylic acids with $\alpha,\beta$-ethylenic unsaturation, $C_4$–$C_6$ dicarboxylic acids with $\alpha,\beta$-ethylenic unsaturation, and monoester and monoamide derivatives of the diacids.

This thickener can be chosen in particular from those disclosed and prepared in U.S. Pat. No. 5,736,125, which is explicitly incorporated herein by reference.

The hydrophobic unit or units of the lipophilic thickening copolymer can be formed from entities chosen from $C_{10}$–$C_{22}$ alkyl (meth)acrylates; ($C_{10}$–$C_{22}$ alkyl)(meth) acrylamides; $C_{10}$–$C_{22}$ vinyl esters and ethers; siloxanes; $C_{10}$–$C_{22}$ $\alpha$-olefins; fluorinated aliphatic side chains with at least 6 carbon atoms; or aliphatic side chains of ($C_1$–$C_{24}$ alkyl)styrene with at least 6 carbon atoms and more particularly of $C_{18}$–$C_{22}$ (meth)acrylates. The hydrophobic unit or units generally represent from 80 to 98% by weight and, in another embodiment, from 85 to 97% of the total weight of the lipophilic thickening copolymer.

The hydrophilic unit or units of the lipophilic thickening copolymer, needed to thicken the oily phase, can be composed of or, as appropriate, derived from, acrylic acid, methacrylic acid, maleic acid or itaconic acid or their monoesters thereof with $C_1$–$C_{22}$ alcohols or monoamides thereof with $C_1$–$C_{22}$ amines and more particularly of acrylic acid and/or methacrylic acid.

The lipophilic thickening copolymers in accordance with the invention generally have an acid number ranging from 0.1 to 4.0 meq/g and more particularly from 0.4 to 2 meq/g. Their average molecular weight, generally, is at least 50,000 Daltons and in another embodiment varies from 50,000 to 200,000 Daltons. This molecular weight is a weight-average molecular weight.

The particularly preferred lipophilic thickening copolymers are chosen from $C_{10}$–$C_{22}$ alkyl (meth)acrylate/(meth)

acrylic acid copolymers in which the amount of alkyl (meth)acrylate is sufficient to obtain the partial or complete solubility of the polymer in an oily phase and the amount of (meth)acrylic acid is sufficient to thicken the oily phase.

They are more particularly still chosen from:

docosyl acrylate/styrene/acrylic acid copolymers in which the amount of docosyl acrylate and styrene monomeric units in the copolymer is sufficient to obtain partial or complete solubility of the resulting polymer in an oily phase and the amount of acrylic acid monomeric unit in the polymer is sufficient to thicken the oily phase, such as the products disclosed under the names Sample 124–93 (72/4/2% by weight), Sample 124–130 (68/2715% by weight) or Sample 108–195 (6712815% by weight) in U.S. Pat. No. 5,736,125 and manufactured by the Company Landec Corporation; and/or stearyl acrylate/methacrylic acid copolymers in which the amount of stearyl acrylate monomeric unit in the copolymer is sufficient to obtain partial or complete solubility of the polymer in an oily phase and the amount of methacrylic acid monomeric unit in the copolymer is sufficient to thicken the oily phase, such as the products disclosed under the names Sample 124–194 (92.5/7.5% by weight) or Sample 124–195 (90/10% by weight) in U.S. Pat. No. 5,736,125 and manufactured by the Company Landec Corporation.

In the context of the present invention, it is very clearly possible to use a mixture of several lipophilic thickening copolymers as defined above.

The lipophilic thickening copolymers can be present in the cosmetic or dermatological compositions of the invention in concentrations preferably ranging from 0.1 to 10% by weight with respect to the total weight of the composition and, in another embodiment, from 0.5 to 2% by weight.

The viscosity of the oily phase is generally of the order of 6000 to 20,000 centipoises (6–20 Pa·s), measured with a Brookfield viscometer, needle 5, at a speed of 20 revolutions/minute.

The fatty phase of the emulsion can comprise any oil capable of being used in the field of application under consideration. This is because one of the advantages relating to the use of the above lipophilic thickening copolymer is that it makes it possible to thicken any oil, whatever its chemical nature.

The term "oil" is understood to mean any fatty substance which is liquid at room temperature (25° C.).

The fatty phase can therefore comprise one or more oils preferably chosen from:

optionally organomodified, volatile and nonvolatile, linear, branched and cyclic silicone oils; phenylated silicones; and silicone resins and gums which are liquid at room temperature;

mineral oils, such as liquid paraffin and liquid petrolatum, oils of animal origin, such as perhydrosqualene and lanolin;

oils of vegetable origin, such as liquid triglycerides, for example sunflower, maize, soybean, jojoba, cucumber, grape seed, sesame, hazelnut, apricot, macadamia, avocado, sweet almond or castor oils, triglycerides of caprylic/capric acids, such as those sold by the company Stearineries Dubois or those sold under the names Miglyol 810, 812 and 818® by the company Dynamit Nobel, olive oil, groundnut oil, rapeseed oil or coconut oil;

synthetic oils, such as purcellin oil, isoparaffins, fatty alcohols or fatty acid esters;

fluorinated and perfluorinated oils;

fluorinated silicone oils;

their mixtures.

The emulsion according to the invention can comprise 1 to 50% by weight of fatty phase, in another embodiment, 5 to 30% by weight and in yet another embodiment, 10 to 20% by weight of fatty phase.

In a known way, the emulsion according to the invention can optionally comprise a small amount of a surfactant, in particular an O/W surfactant, although this is not necessary to obtain a stable emulsion. The amount of surfactant can represent from 0.1 to 3% and preferably from 0.1 to 2% of the total weight of the emulsion. Advantageously, the emulsion does not comprise surfactant.

The emulsion according to the invention can be used in particular in the cosmetics and/or dermatological fields. It can be used as is and thus itself constitute a cosmetic or dermatological composition; it can also be incorporated in a more sophisticated cosmetic or dermatological composition.

The compositions according to the invention, composed of or comprising the emulsion, comprise a cosmetically or dermatologically acceptable medium, that is to say a medium compatible with all keratinous substances, such as the skin, nails, mucous membranes and hair or any other cutaneous region of the body. This medium can comprise, in a way known per se, the constituents conventionally employed in the field of application under consideration.

In particular, these compositions can comprise:

waxes chosen from animal, fossil, vegetable, mineral and synthetic waxes known per se, such as paraffin waxes, polyethylene waxes, carnauba and candelilla waxes, beeswaxes, microcrystalline wax and silicone waxes;

organic solvents;

hydrophilic and lipophilic cosmetic and dermatological active principles, such as softeners, antioxidants, opacifiers, emollients, hydroxy acids, antifoaming agents, moisturizers, vitamins, fragrances, preservatives, dyes, sequestering agents, polymers, propellants, basifying or acidifying agents, UV screening agents, ceramides, agents for combating free radicals, slimming agents, bactericides, antidandruff agents, complexing agents and odour absorbers;

pulverulent materials, such as fillers, pigments and pearlescent agents.

These adjuvants, depending on their nature, can be introduced into the fatty phase or into the aqueous phase. Of course, a person skilled in the art will take care to choose this or these optional additional compounds and/or their amount so that the advantageous properties of the composition according to the invention are not, or not substantially, detrimentally affected by the envisaged addition.

The emulsion and the composition according to the invention can be prepared according to techniques known to a person skilled in the art.

In particular, the emulsion can be prepared by dissolving the lipophilic thickening copolymer in the fatty phase heated to 60–80° C., by then dissolving the hydrophilic thickener in the aqueous phase heated to 60–80° C., and by dispersing the fatty phase in the aqueous phase with stirring.

The compositions according to the invention can be provided in the form of a suspension or a dispersion in the fatty substances; in the form of a nonionic vesicular dispersion; in the form of a simple or complex emulsion (O/W, W/O, O/W/O or W/O/W), preferably of oil-in-water type; a cream, a milk, a gel, an ointment, an aerosol foam or a spray; a serum or a paste.

They find an application in particular in a great number of cosmetic or dermatological treatments of the skin, hair, eyelashes, eyebrows, nails, mucous membranes or scalp; mention may in particular be made of caring for the face and/or body (protection, treatment or care creams for the face, for the hands or for the body; protection or care body milks; or lotions, gels or foams for caring for the skin and mucous membranes or for cleansing the skin); making up the face and/or body (lipstick, eyeliner, foundation, mascara, concealer, eye shadow or face powder); removing make-up; antisun protection; or the dermatological treatment of diseases of the skin, hair, eyelashes, eyebrows, nails, scalp and/or mucous membranes.

They find a preferred application in cosmetic or dermatological compositions intended for dry and/or sensitive skin.

The invention is illustrated in more detail in the following examples, in which the % are given by weight.

EXAMPLE 1

Nourishing Cream for Very Dry Skin

| Phase A | |
| --- | --- |
| Crosslinked poly(2-acrylamido-2-methyl-propanesulphonic acid) (Example A of EP 815,844), at 2% in water | 1.5% |
| Glycerol | 5% |
| Preservatives | 0.3% |
| Water q.s. for | 100% |

| Phase B | |
| --- | --- |
| Apricot kernel oil | 25% |
| Hydrogenated isoparaffin | 10% |
| Stearyl acrylate/methacrylic acid (92.5/7.5% by weight) copolymer corresponding to "Sample 124–194" in U.S. Pat. No. 5,736,125 | 1% |

The emulsion is prepared in the following way: phases A and B are prepared by simple mixing under warm conditions of the constituents and are homogenized separately with stirring at 70–75° C. The fatty phase B is then dispersed with stirring in the aqueous phase A.

A fine and even emulsion is obtained, the edges of which are sharp. The emulsion remains stable for at least two months at a temperature of 20° C. and at a temperature of 37° C.

EXAMPLE 2

Rich Cream for Caring for the Body

| Phase A | |
| --- | --- |
| Crosslinked poly(2-acrylamido-2-methyl-propanesulphonic acid) (Example A of EP 815,844), at 2% in water | 1% |
| Glycerol | 5% |
| Preservatives | 0.3% |
| Water q.s. for | 100% |

| Phase B | |
| --- | --- |
| Liquid petrolatum | 15% |
| Myristyl myristate | 10% |
| Stearyl acrylate/methacrylic acid (92.5/7.5% by weight) copolymer corresponding to "Sample 124–194" in U.S. Pat. No. 5,736,125 | 1% |

The emulsion is prepared according to Example 1. A fine and supple emulsion which is easy to apply is obtained. It is soft and nourishing. It exhibits good stability at 20° C., 37° C. and 45° C. for at least two months.

EXAMPLE 3

Fluid Facial Make-up Remover for Sensitive Skin

| Phase A | |
| --- | --- |
| Acrylate/$C_{10}$—$C_{30}$ alkyl acrylate copolymer (Pemulen TR 2) | 0.2% |
| Preservatives | 0.3% |
| Water q.s. for | 100% |

| Phase B | |
| --- | --- |
| Octyl palmitate | 20% |
| Stearyl acrylate/methacrylic acid (92.5/7.5% by weight) copolymer corresponding to "Sample 124–194" in U.S. Pat. No. 5,736,125 | 0.5% |

The emulsion is prepared according to Example 1. A supple and light emulsion is obtained which exhibits a very good make-up removing power without attacking the skin.

EXAMPLE 4

The following emulsions are compared under the microscope:

Emulsion A according to Example 1

Emulsion B: emulsion according to Example 1 without stearyl acrylate/methacrylic acid copolymer Emulsion C: emulsion according to Example 1, in which the stearyl acrylate/methacrylic acid copolymer has been replaced by glyceryl stearate.

The following results are obtained:

Emulsion A is fine and even and the edges are sharp.

Emulsion B is coarse under the microscope. It is unstable and breaks down on the very day of manufacture. Poor stability is obtained, in particular because the level of fatty phase is too high. Beyond approximately 15% of liquid fatty phase, the crosslinked poly(2-acrylamido-2-methylpropanesulphonic acid), known for stabilizing emulsions, is no longer sufficient to give a stable emulsion.

Emulsion C is very coarse under the microscope and the edges are very "loose". It is unstable and "phase separation" is rapid. The emulsion slides over the walls of the bottle, which also shows its instability: it is oily. Furthermore, the cosmetic properties of Emulsion C are inferior to those of Emulsion A: texture less smooth, greasy, not fresh.

What is claimed is:

1. An emulsion composition, comprising:
an aqueous phase;
an oily phase;
at least one hydrophilic thickening compound; and
at least one lipophilic thickening copolymer which contains at least one hydrophobic unit in an amount sufficient to achieve partial or complete solubility in said oily phase and at least one hydrophilic unit in an amount sufficient to produce thickening of said oily phase;
wherein said hydrophilic unit is formed from entities chosen from: $C_3$–$C_6$ monocarboxylic acids with $\alpha,\beta$-ethylenic unsaturation, $C_4$–$C_6$ dicarboxylic acids with $\alpha,\beta$-ethylenic unsaturation, and the monoester and monoamide derivatives of $C_4$–$C_6$ dicarboxylic acids with $\alpha,\beta$-ethylenic unsaturation;
wherein said at least one hydrophilic thickening compound is chosen from:
polysaccharide biopolymers;
aluminium magnesium silicates;
polyacrylic acids chosen from poly(glyceryl(meth)acrylate) polymers, acrylic acid homopolymers, which may or may not be crosslinked, and salts thereof;
polyacrylamide-based polymers;
copolymers which may or may not be crosslinked, containing:
a major fraction of monomeric units originating from monomers chosen from mono-olefinically unsaturated $C_3$–$C_6$ carboxylic acid monomers and of mono-olefinically unsaturated $C_3$–$C_6$ carboxylic anhydride;
a minor fraction of monomeric units originating from monomers chosen from esters with a fatty chain of acrylic acid monomer;
crosslinked poly(2-acrylamido-2-methyl-propanesulphonic acid) polymers which may be substantially or completely neutralized, containing randomly distributed:
units of formula (1):

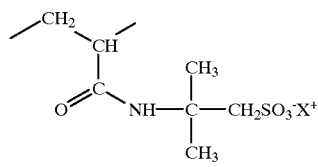

(1)

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;
crosslinking units produced from at least one monomer having at least two olefinic double bonds, wherein said crosslinking units are present in an amount ranging from 0.01 to 10% by weight of said crosslinked poly (2-acrylamido-2-methyl-propanesulphonic acid) polymers; and
inorganic thickeners chosen from smectites and hectorites, which may be modified or unmodified.

2. The emulsion composition according to claim 1, wherein said at least one hydrophobic unit of said at least one lipophilic thickening copolymer is formed from entities chosen from $C_{10}$–$C_{22}$ alkyl (meth)acrylates, ($C_{10}$–$C_{22}$ alkyl) (meth)acrylamides; $C_{10}$–$C_{22}$ vinyl esters, $C_{10}$–$C_{22}$ vinyl ethers, siloxanes, $C_{10}$–$C_{22}$ α-olefins, fluorinated aliphatic side chains with at least 6 carbon atoms, and aliphatic side chains of ($C_1$–$C_{24}$ alkyl)styrenes with at least 6 carbon atoms.

3. The emulsion composition according to claim 2, wherein said at least one hydrophobic unit of said at least one lipophilic thickening copolymer is formed from $C_{18}$–$C_{22}$ (meth)acrylates.

4. The emulsion composition according to claim 1, wherein said at least one hydrophobic unit of said at least one lipophilic thickening copolymer is present in an amount ranging from 80 to 98% by weight of the total weight of said at least one lipophilic thickening copolymer.

5. The emulsion composition according to claim 4, wherein said amount ranges from 85 to 97%.

6. The emulsion composition according to claim 1, wherein said at least one hydrophilic unit of said at least one lipophilic thickening copolymer is formed from entities chosen from acrylic acid, methacrylic acid, maleic acid, itaconic acid, monoesters thereof with $C_1$–$C_{22}$ alcohols, and monoamides thereof with $C_1$–$C_{22}$ amines.

7. The emulsion composition according to claim 6, wherein said at least one hydrophilic unit of said at least one lipophilic thickening copolymer is formed from entities chosen from acrylic acid and methacrylic acid.

8. The emulsion composition according to claim 1, wherein said at least one lipophilic thickening copolymer is chosen from $C_{10}$–$C_{22}$ alkyl (meth)acrylate/(meth)acrylic acid copolymers.

9. The emulsion composition according to claim 8, wherein said at least one lipophilic thickening copolymer is chosen from docosyl acrylate/styrene/acrylic acid copolymers and stearyl acrylate/methacrylic acid copolymers.

10. The emulsion composition according to claim 1, wherein said at least one lipophilic thickening copolymer is present in an amount ranging from 0.1 to 10% by weight with respect to the total weight of said emulsion composition.

11. The emulsion composition according to claim 10, wherein said amount ranges from 0.5 to 2%.

12. The emulsion composition according to claim 1, wherein said at least one lipophilic thickening copolymer has an average molecular weight of at least 50,000 Daltons.

13. The emulsion composition according to claim 1, wherein said polysaccharide biopolymers are chosen from: xanthan gum, locust bean gum, guar gum, alginates and modified celluloses.

14. The emulsion composition according to claim 13, wherein said modified celluloses are chosen from hydroxyethylcellulose, methylcellulose, hydroxypropylcellulose, and carboxymethylcellulose.

15. The emulsion composition according to claim 1, wherein said polyacrylamide-based polymers are chosen from:

oil-in-water emulsions comprising from 35 to 45% by weight of crosslinked neutralized acrylamide/2-acrylamido-2-methylpropanesulphonic acid copolymers, from 15 to 25% by weight of isoparaffin hydrocarbons, from 3 to 8% by weight of polyethylene glycol 7EO lauryl ether, and water;

acrylate/octylacrylamide copolymers;

crosslinked polymers of methacryloyloxyethyltrimethylammonium chloride and of acrylamide;

crosslinked polymers of acrylamide and of ammonium acrylate; and crosslinked poly(2-acrylamido-2-methylpropanesulphonic acid) polymers which may be substantially or completely neutralized.

16. The emulsion composition according to claim 1, wherein said at least one hydrophilic thickening compound is present an amount ranging from 0.05 to 10% by weight with respect to the total weight of said emulsion composition.

17. The emulsion composition according to claim 16, wherein said amount ranges from 0.5 to 4%.

18. The emulsion composition according to claim 1, wherein said emulsion composition has a form chosen from oil-in-water emulsions comprising an internal fatty or oily phase dispersed in an external aqueous phase.

19. The emulsion composition according to claim 1, wherein said oily phase further comprises at least one ingredient chosen from:

volatile and nonvolatile, linear, branched and cyclic silicone oils which may or may not be organomodified; phenylated silicones; and silicone resins and gums which are liquid at room temperature; mineral oils;

oils having an origin chosen from animal, vegetable and synthetic origin;

fluorinated and perfluorinated oils; and fluorinated silicone oils.

20. The emulsion composition according to claim 19, wherein said oils are chosen from:

mineral oils chosen from liquid paraffin and liquid petrolatum;

oils of animal origin chosen from perhydrosqualene and lanolin;

oils of vegetable origin chosen from liquid triglycerides; and synthetic oils chosen from purcellin oil, isoparaffins, fatty alcohols and fatty acid esters.

21. The emulsion composition according to claim 20, wherein said liquid triglycerides are chosen from sunflowers, maizes, soybeans, jojobas, cucumbers, grape seeds, sesames, hazelnuts, apricots, macadamias, avocados, sweet almond oils, castor oils, triglycerides of caprylic/capric acids, olive oils, groundnut oils, rapeseed oils and coconut oils.

22. The emulsion composition according to claim 1, wherein said oily phase is present in an amount ranging from 1 to 50% relative to the total weight of said emulsion composition.

23. The emulsion composition according to claim 22, wherein said amount ranges from 5 to 30%.

24. The emulsion composition according to claim 23, wherein said amount ranges from 10 to 20%.

25. The emulsion composition according to claim 1, wherein said emulsion composition does not comprise a surfactant.

26. A cosmetic of dermatological product, comprising an emulsion comprising:

an aqueous phase;

an oily phase;

at least one hydrophilic thickening compound; and at least one lipophilic thickening copolymer which contains at least one hydrophobic unit in an amount sufficient to achieve partial or complete solubility in said oily phase and at least one hydrophilic unit in an amount sufficient to produce thickening of said oily phase;

wherein said hydrophilic unit is formed from entities chosen from: $C_3$–$C_6$ monocarboxylic acids with α,β-ethylenic unsaturation, $C_4$–$C_6$ dicarboxylic acids with α,β-ethylenic unsaturation, and the monoester and monoamide derivatives of $C_4$–$C_6$ dicarboxylic acids with α,β-ethylenic unsaturation;

wherein said at least one hydrophilic thickening compound is chosen from:

polysaccharide biopolymers;

aluminium magnesium silicates;

polyacrylic acids chosen from poly(glyceryl(meth)acrylate) polymers, acrylic acid homopolymers, which may or may not be crosslinked, and salts thereof;

polyacrylamide-based polymers;

copolymers which may or may not be crosslinked, containing:

a major fraction of monomeric units originating from monomers chosen from mono-olefinically unsaturated $C_3$–$C_6$ carboxylic acid monomers and of mono-olefinically unsaturated $C_3$–$C_6$ carboxylic anhydride;

a minor fraction of monomeric units originating from monomers chosen from esters with a fatty chain of acrylic acid monomer;

crosslinked poly(2-acrylamido-2-methyl-propanesulphonic acid) polymers which may be substantially or completely neutralized, containing randomly distributed:

units of formula (1):

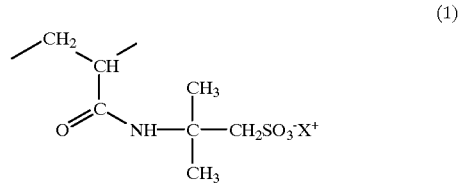

(1)

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;

crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers; and inorganic thickeners chosen from smectites and hectorites, which may be modified unmodified.

27. The cosmetic or dermatological product according to claim 26, wherein said cosmetic or dermatological product is chosen from products for caring for the face and body.

28. A process for making a dermatological composition intended for treatment of skin, hair, eyelashes, eyebrows, nails, scalp, or mucous membranes comprising the step of forming said dermatological composition and including therein an emulsion comprising:

an aqueous phase;

an oily phase;

at least one hydrophilic thickening compound; and at least one lipophilic thickening copolymer which contains at least one hydrophobic unit in an amount sufficient to achieve partial or complete solubility in said oily phase and at least one hydrophilic unit in an amount sufficient to produce thickening of said oily phase;

wherein said hydrophilic unit is formed from entities chosen from: $C_3$–$C_6$ monocarboxylic acids with α,β-ethylenic unsaturation, $C_4$–$C_6$ dicarboxylic acids with α,β-ethylenic unsaturation, and the monoester and monoamide derivatives of $C_4$–$C_6$ dicarboxylic acids with α,β-ethylenic unsaturation;

wherein said at least one hydrophilic thickening compound is chosen from:

polysaccharide biopolymers;

aluminium magnesium silicates;

polyacrylic acids chosen from poly(glyceryl(meth)acrylate) polymers, acrylic acid homopolymers, which may or may not be crosslinked, and salts thereof;

polyacrylamide-based polymers;

copolymers which may or may not be crosslinked, containing:

a major fraction of monomeric units originating from monomers chosen from mono-olefinically unsaturated $C_3$–$C_6$ carboxylic acid monomers and of mono-olefinically unsaturated $C_3$–$C_6$ carboxylic anhydride;

a minor fraction of monomeric units originating from monomers chosen from esters with a fatty chain of acrylic acid monomer;

crosslinked poly(2-acrylamido-2-methyl-propanesulphonic acid) polymers which may be substantially or completely neutralized, containing randomly distributed:

units of formula (1):

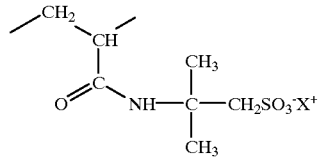

(1)

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;

crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers; and inorganic thickeners chosen from smectites and hectorites, which may be modified or unmodified.

29. A cosmetic or dermatological composition for dry or sensitive skin comprising an emulsion comprising:

an aqueous phase;

an oily phase;

at least one hydrophilic thickening compound; and at least one lipophilic thickening copolymer which contains at least one hydrophobic unit in an amount sufficient to achieve partial or complete solubility in said oily phase and at least one hydrophilic unit in an amount sufficient to produce thickening of said oily phase;

wherein said hydrophilic unit is formed from entities chosen from: $C_3$–$C_6$ monocarboxylic acids with α,β-ethylenic unsaturation, $C_4$–$C_6$ dicarboxylic acids with α,β-ethylenic unsaturation, and the monoester and monoamide derivatives of $C_4$–$C_6$ dicarboxylic acids with α,β-ethylenic unsaturation;

wherein said at least one hydrophilic thickening compound is chosen from:

polysaccharide biopolymers;

aluminium magnesium silicates;

polyacrylic acids chosen from poly(glyceryl(meth)acrylate) polymers, acrylic acid homopolymers, which may or may not be crosslinked, and salts thereof;

polyacrylamide-based polymers;

copolymers which may or may not be crosslinked, containing:

a major fraction of monomeric units originating from monomers chosen from mono-olefinically unsaturated $C_3$–$C_6$ carboxylic acid monomers and of mono-olefinically unsaturated $C_3$–$C_6$ carboxylic anhydride;

a minor fraction of monomeric units originating from monomers chosen from esters with a fatty chain of acrylic acid monomer;

crosslinked poly(2-acrylamido-2-methyl-propanesulphonic acid) polymers which may be substantially or completely neutralized, containing randomly distributed:

units of formula (1):

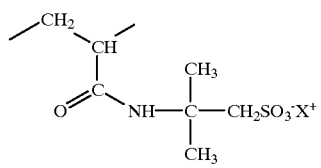

(1)

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;

crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers; and inorganic thickeners chosen from smectites and hectorites, which may be modified or unmodified.

30. A process for a nontherapeutic treatment of the skin, hair, eyelashes, eyebrows, nails, mucous membranes or scalp, comprising: applying to said skin, hair, eyelashes, eyebrows, nails, mucous membranes or scalp an emulsion comprising:

an aqueous phase;

an oily phase;

at least one hydrophilic thickening compound; and at least one lipophilic thickening copolymer which contains at least one hydrophobic unit in an amount sufficient to achieve partial or complete solubility in said oily phase and at least one hydrophilic unit in an amount sufficient to produce thickening of said oily phase;

wherein said hydrophilic unit is formed from entities chosen from: $C_3-C_6$ monocarboxylic acids with $\alpha,\beta$-ethylenic unsaturation, $C_4-C_6$ dicarboxylic acids with $\alpha,\beta$-ethylenic unsaturation, and the monoester and monoamide derivatives of $C_4-C_6$ dicarboxylic acids with $\alpha,\beta$-ethylenic unsaturation;

wherein said at least one hydrophilic thickening compound is chosen from:

polysaccharide biopolymers;

aluminium magnesium silicates;

polyacrylic acids chosen from poly(glyceryl(meth)acrylate) polymers, acrylic acid homopolymers, which may or may not be crosslinked, and salts thereof;

polyacrylamide-based polymers;

copolymers which may or may not be crosslinked, containing:
a major fraction of monomeric units originating from monomers chosen from mono-olefinically unsaturated $C_3-C_6$ carboxylic acid monomers and of mono-olefinically unsaturated $C_3-C_6$ carboxylic anhydride;
a minor fraction of monomeric units originating from monomers chosen from esters with a fatty chain of acrylic acid monomer;

crosslinked poly(2-acrylamido-2-methyl-propanesulphonic acid) polymers which may be substantially or completely neutralized, containing randomly distributed:

units of formula (1):

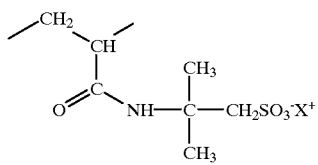

(1)

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;

crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers; and inorganic thickeners chosen from smectites and hectorites, which may be modified or unmodified.

31. A process for a nontherapeutic treatment of dry or sensitive skin, comprising applying to said skin an emulsion comprising:

an aqueous phase;

an oily phase;

at least one hydrophilic thickening compound; and at least one lipophilic thickening copolymer which contains at least one hydrophobic unit in an amount sufficient to achieve partial or complete solubility in said oily phase and at least one hydrophilic unit in an amount sufficient to produce thickening of said oily phase;

wherein said hydrophilic unit is formed from entities chosen from: $C_3-C_6$ monocarboxylic acids with $\alpha$-ethylenic unsaturation, $C_4-C_6$ dicarboxylic acids with $\alpha,\beta$-ethylenic unsaturation, and the monoester and monoamide derivatives of $C_4-C_6$ dicarboxylic acids with $\alpha,\beta$-ethylenic unsaturation;

wherein said at least one hydrophilic thickening compound is chosen from:

polysaccharide biopolymers;

aluminium magnesium silicates;

polyacrylic acids chosen from poly(glyceryl(meth)acrylate) polymers, acrylic acid homopolymers, which may or may not be crosslinked, and salts thereof;

polyacrylamide-based polymers;

copolymers which may or may not be crosslinked, containing:
a major fraction of monomeric units originating from monomers chosen from mono-olefinically unsaturated $C_3-C_6$ carboxylic acid monomers and of mono-olefinically unsaturated $C_3-C_6$ carboxylic anhydride;
a minor fraction of monomeric units originating from monomers chosen from esters with a fatty chain of acrylic acid monomer;

crosslinked poly(2-acrylamido-2-methyl-propanesulphonic acid) polymers which may be substantially or completely neutralized, containing randomly distributed:

units of formula (1):

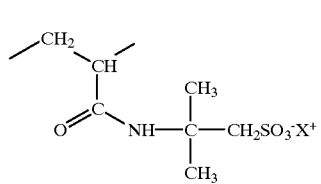

(1)

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;

crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers; and inorganic thickeners chosen from smectites and hectorites, which may be modified or unmodified.

32. A method of stabilizing an emulsion comprising an aqueous phase and an oily phase, comprising including in said emulsion:

at least one hydrophilic thickening compound; and at least one lipophilic thickening copolymer which contains at least one hydrophobic unit in an amount sufficient to achieve partial or complete solubility in said oily phase and at least one hydrophilic unit in an amount sufficient to produce thickening of said oily phase;
  wherein said hydrophilic unit is formed from entities chosen from: $C_3$–$C_6$ monocarboxylic acids with $\alpha,\beta$-ethylenic unsaturation, $C_4$–$C_6$ dicarboxylic acids with $\alpha,\beta$-ethylenic unsaturation, and the monoester and monoamide derivatives of $C_4$–$C_6$ dicarboxylic acids with $\alpha,\beta$-ethylenic unsaturation;
  wherein said at least one hydrophilic thickening compound is chosen from:
  polysaccharide biopolymers;
  aluminium magnesium silicates;
polyacrylic acids chosen from poly(glyceryl(meth)acrylate) polymers, acrylic acid homopolymers, which may or may not be crosslinked, and salts thereof;
polyacrylamide-based polymers;
copolymers which may or may not be crosslinked, containing:
  a major fraction of monomeric units originating from monomers chosen from mono-olefinically unsaturated $C_3$–$C_6$ carboxylic acid monomers and of mono-olefinically unsaturated $C_3$–$C_6$ carboxylic anhydride;
  a minor fraction of monomeric units originating from monomers chosen from esters with a fatty chain of acrylic acid monomer;
crosslinked poly(2-acrylamido-2-methyl-propanesulphonic acid) polymers which may be substantially or completely neutralized, containing randomly distributed:
units of formula (1):

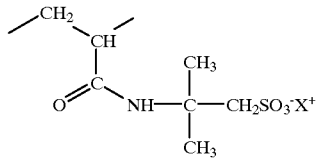

in which: $X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers;

crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers; and inorganic thickeners chosen from smectites and hectorites, which may be modified or unmodified.

33. The method according to claim 32, wherein said emulsion is an oil-in-water emulsion.

34. The method according to claim 32, wherein said emulsion does not comprise a surfactant.

* * * * *